US009942225B2

(12) United States Patent
Navratil et al.

(10) Patent No.: US 9,942,225 B2
(45) Date of Patent: *Apr. 10, 2018

(54) USER AUTHENTICATION VIA EVOKED POTENTIAL IN ELECTROENCEPHALOGRAPHIC SIGNALS

(71) Applicant: International Business Machines Corporation, Armonk, NY (US)

(72) Inventors: Jiri Navratil, Cortlandt Manor, NY (US); Bhuvana Ramabhadran, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/867,551

(22) Filed: Sep. 28, 2015

(65) Prior Publication Data

US 2016/0021106 A1 Jan. 21, 2016

Related U.S. Application Data

(63) Continuation of application No. 14/710,058, filed on May 12, 2015, now Pat. No. 9,226,698, which is a (Continued)

(51) Int. Cl.
*H04L 29/06* (2006.01)
*G06F 21/32* (2013.01)
(Continued)

(52) U.S. Cl.
CPC ...... *H04L 63/0861* (2013.01); *A61B 5/04842* (2013.01); *A61B 5/117* (2013.01); *G06F 21/32* (2013.01); *H04L 67/306* (2013.01)

(58) Field of Classification Search
CPC .... H04L 63/0861; H04L 67/306; G06F 21/32
See application file for complete search history.

(56) References Cited

U.S. PATENT DOCUMENTS 5,163,444 A 11/1992 Braverman
5,719,950 A * 2/1998 Osten et al. ......... A61B 5/0205
340/5.82

(Continued)

OTHER PUBLICATIONS

Marcel et al., ("Person Authentication Using Brainwaves (EEG) and Maximum A Posteriori Model Adaptation", Apr. 2007, IEEE Transactions on Pattern Analysis and Machine Intelligence, pp. 743-752.*

(Continued)

*Primary Examiner* — Kenneth Chang
(74) *Attorney, Agent, or Firm* — David M. Quinn; Ryan, Mason & Lewis, LLP

(57) ABSTRACT

Techniques are disclosed for authentication and identification of a user by use of an electroencephalographic (EEG) signal. For example, a method for authenticating a user includes the following steps. At least one electroencephalographic response is obtained from a user in accordance with perceptory stimuli presented to the user. The user is authenticated based on the obtained electroencephalographic response. The authenticating step may be based on detection of an event-related potential in the obtained electroencephalographic response. The event-related potential may be a P300 event-related potential. The method may also include the step of enrolling the user prior to authenticating the user. The enrolling step may include a supervised enrollment procedure or an unsupervised enrollment procedure.

20 Claims, 8 Drawing Sheets

Related U.S. Application Data continuation of application No. 11/846,893, filed on Aug. 29, 2007, now Pat. No. 9,058,473.

(51) Int. Cl.
*A61B 5/0484* (2006.01)
*A61B 5/117* (2016.01)
*H04L 29/08* (2006.01)

(56) References Cited

U.S. PATENT DOCUMENTS

| | | | | |
|---|---|---|---|---|
| 6,510,340 | B1* | 1/2003 | Jordan | A61B 5/0478 600/383 |
| 7,249,263 | B2 | 7/2007 | Chaudhari et al. | |
| 7,647,098 | B2 | 1/2010 | Prichep | |
| 7,885,700 | B2* | 2/2011 | Clark | G01R 5/28 600/372 |
| 7,899,915 | B2* | 3/2011 | Reisman | G06F 17/30873 709/227 |
| 2005/0022034 | A1* | 1/2005 | Chaudhari et al. | G06F 21/32 726/19 |
| 2006/0056662 | A1* | 3/2006 | Thieme et al. | G06K 9/00067 382/115 |
| 2006/0078172 | A1* | 4/2006 | Zhang et al. | G06K 9/00268 382/118 |
| 2007/0100251 | A1* | 5/2007 | Prichep | A61B 5/04009 600/544 |
| 2008/0004904 | A1* | 1/2008 | Tran | A61B 5/0006 705/2 |
| 2008/0005578 | A1 | 1/2008 | Shafir | |
| 2008/0154148 | A1 | 6/2008 | Chung et al. | |
| 2008/0194981 | A1 | 8/2008 | Sarkela et al. | |
| 2008/0229408 | A1 | 9/2008 | Dinges et al. | |
| 2008/0294907 | A1 | 11/2008 | Hively | |
| 2009/0063866 | A1 | 3/2009 | Navratil et al. | |

OTHER PUBLICATIONS

Fish & Spehlmann's, "EEG Primer," Elsevier, 3rd Edition, Dec. 17, 1999, pp. 16-19, 31-37, and 76-79.

H.Ö. Gülçür et al., "Classification of P300 Component in Single Trial Event Related Potentials," 2nd IEEE International Conference on Biomedical Engineering Days, May 1998, pp. 48-50, Istanbul, Turkey.

R.Q. Quiroga et al., "Wavelet Entropy in Event-Related Potentials: a New Method Shows Ordering of EEG Oscillations," Biological Cybernetics, Apr. 2001, pp. 291-299, vol. 84, No. 4.

P.O. Ranta-Aho et al., "Single-Trial Estimation of Multichannel Evoked-Potential Measurements," IEEE Transactions on Biomedical Engineering, Feb. 2003, pp. 189-196, vol. 50, No. 2.

* cited by examiner

USER AUTHENTICATION VIA EVOKED POTENTIAL IN ELECTROENCEPHALOGRAPHIC SIGNALS

CROSS-REFERENCE TO RELATED APPLICATIONS

This application is a Continuation of U.S. patent application Ser. No. 14/710,058, filed on May 12, 2015, now U.S. Pat. No. 9,226,698, which is a Continuation of U.S. patent application Ser. No. 11/846,893, filed on Aug. 29, 2007, now U.S. Pat No. 9,058,473, the disclosures of which are incorporated herein by reference.

FIELD OF THE INVENTION

The present invention generally relates to user authentication techniques and, more particularly, to techniques that determine authentication and identification of a user by use of an electroencephalographic signal.

BACKGROUND OF THE INVENTION

Authenticating (identifying) users from various signals and modalities plays an important role in securing data and applications and in authorizing specific sets of identities to gain access. All authentication solutions draw information from at most three categories: biometrics, possession and knowledge. The latter is usually implemented as an authentication interview in which knowledge is communicated in some way (written text, spoken word), a classic example being a user personal identification number (PIN).

Knowledge-based authentication is prone to imposter attacks combined with so-called "social engineering," i.e., various ways to acquire the knowledge necessary to pass the authentication (e.g., "shoulder surfing," guessing passwords, etc.), the main weakness of this type of authentication. Possession-based authentication (e.g., door key or some other identifying device) and biometric-based authentication (e.g., fingerprint) are also prone to fraud.

SUMMARY OF THE INVENTION

Principles of the invention provide techniques for authentication of a user by use of an electroencephalographic (EEG) signal.

For example, in one aspect of the invention, a method for authenticating a user includes the following steps. At least one electroencephalographic response is obtained from a user in accordance with perceptory stimuli presented to the user. The user is authenticated based on the obtained electroencephalographic response. The authenticating step may be based on detection of an event-related potential in the obtained electroencephalographic response. The event-related potential may be a P300 event-related potential.

The method may also include the step of enrolling the user prior to authenticating the user. The enrolling step may include presenting the user with a first set of perceptory stimuli, recording a first set of electroencephalographic responses of the user to the first set of perceptory stimuli, and analyzing the first set of recorded electroencephalographic responses to generate a first set of results. The consistency of the first set of results may be confirmed by repeating the enrolling step.

In an illustrative embodiment, the enrolling step includes a supervised enrollment procedure. In such a procedure, the first set of perceptory stimuli includes one or more perceptory stimuli that follow an explicit rule and one or more perceptory stimuli that violate the explicit rule. The user is informed of the explicit rule before being presented with the first set of perceptory stimuli. The first set of electroencephalographic responses includes a P300 event-related potential corresponding to the occurrence of a violation of the explicit rule.

In another illustrative embodiment, the enrolling step includes an unsupervised enrollment procedure. In such a procedure, the user is presented with a training set of perceptory stimuli prior to being presented with the first set of perceptory stimuli, wherein the training set includes perceptory stimuli from which one or more rules may be interpreted. The user is not informed of the one or more rules that may be interpreted from the training set of perceptory stimuli. The user selects one of the one or more rules that may be interpreted from the training set of perceptory stimuli. The first set of perceptory stimuli includes one or more perceptory stimuli that follow the selected one of the one or more rules and one or more perceptory stimuli that violate the selected one of the one or more rules. The first set of electroencephalographic responses includes a P300 event-related potential corresponding to the occurrence of a violation of the selected one of the one or more rules.

The authenticating step of the method may further include presenting the user with a second set of perceptory stimuli, recording a second set of electroencephalographic responses of the user to the second set of perceptory stimuli, analyzing the second set of recorded electroencephalographic responses to generate a second set of results, and making an authentication decision based on a comparison of the first set of results and the second set of results. The comparison of the first set of results and the second set of results may include time-aligning the first set of results and the second set of results.

These and other objects, features and advantages of the present invention will become apparent from the following detailed description of illustrative embodiments thereof, which is to be read in connection with the accompanying drawings.

DETAILED DESCRIPTION OF PREFERRED EMBODIMENTS

Illustrative embodiments of the invention will be described below in the context of systems that determine the authenticity of a user by extracting their knowledge encoded in the electroencephalographic (EEG) signal. That is, principles of the invention improve the user authentication process by making use of the so-called Brain-Computer-Interface (BCI) which is established through the EEG signal. By authenticating the user via the EEG signal using perceptory knowledge, such as visual (pictorial) or auditory knowledge, that may not necessarily be expressed in a verbal form (or may be hard to communicate in general), an eavesdropper is prevented from gaining the essential secret information.

The term "perceptory" as used herein is generally defined as something that is "perceived" or "perceivable" by one or more of the human senses (e.g., vision, hearing, etc.).

Before describing illustrative embodiments of the invention, we provide a brief description of the neuroscientific background associated with EEG signals.

Figure 1A:
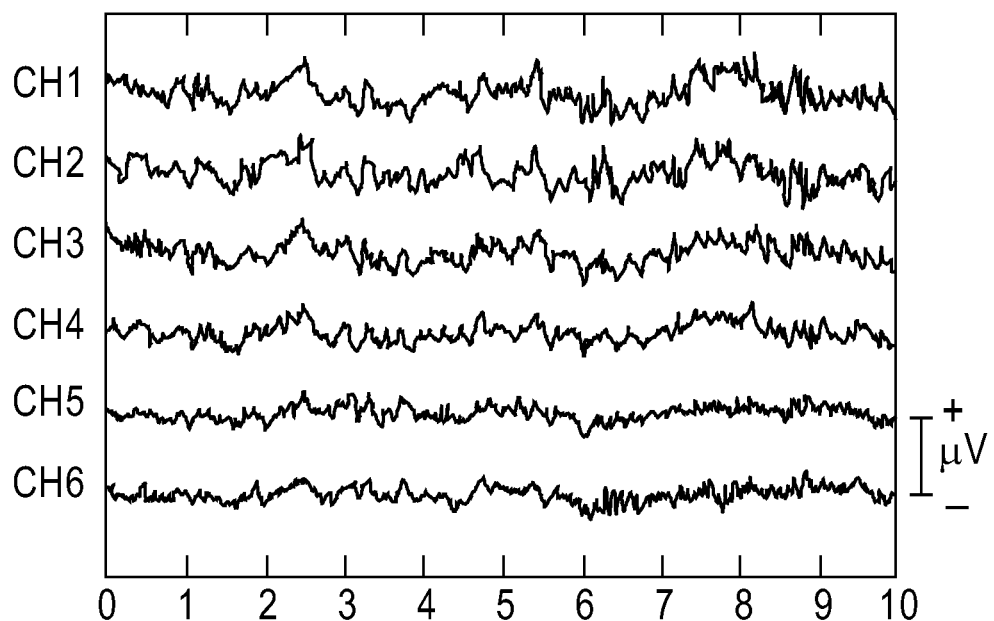
FIG. 1A shows an example of recorded EEG signals.

The electrical nature of the human nervous system has been recognized for over a century. It is well known that the variation of the surface potential distribution on the scalp of an individual reflects functional activities emerging from the underlying brain. This surface potential variation can be recorded by affixing an array of electrodes to the scalp, and measuring the voltage between pairs of these electrodes. These voltage signals are then filtered, amplified and recorded. The resulting data is called the electroencephalogram (or simply EEG). FIG. 1A shows waveforms of a ten second EEG segment containing six recording channels (CH1 through CH6). The voltage between channels is in the microvolt ($\mu V$) range.

Figure 1B:
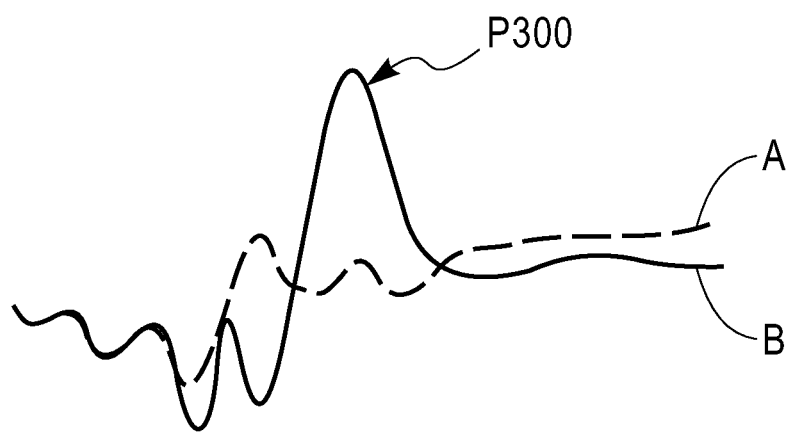
FIG. 1B shows an example of a recorded event-related potential referred to as the P300 signal.

Further, it is known that so-called event-related potentials (ERPs) may be derived from EEG recordings that are time-locked to a stimulus event. The ERPs represent the responses of a brain during sensory and cognitive processing. One such ERP is known as the P300 potential. P300 is a visual/auditory-evoked potential and presents itself in an EEG as a prominent peak detectable after about 300 milliseconds (ms) following a specific visual or auditory stimulus. P300 is a consistent phenomenon in human EEG. When a human subject is presented with a sequence of sounds or pictures that follow a certain well defined logic, the P300 can be detected after an event in the sequence which does not follow that logic, i.e., the event is in that sense "surprising" to the subject. As shown in FIG. 1B, the dashed line (A) represents part of an EEG signal associated with an event that follows expected logic, while the solid line (B) represents part of an EEG signal associated with an event that does not follow expected logic. Note that in the EEG signal labeled B, a P300 peak is present, indicative of the fact that the event in some way "surprised" the subject.

It is also known that the P300 signal only peaks in the vicinity of 300 ms for very simple decisions. More generally, its latency appears to reflect the amount of time necessary to come to a decision about the stimulus. The harder the decision, the longer it takes for the P300 to appear. The leading theory, referred to as the context updating hypothesis, is that it reflects an updating of expectancies about how probable events are in the current context. Because this updating can not be conducted until the stimulus has been categorized, its latency is dependent on how long it took to come to the decision. One of its useful properties is that, unlike measure of physical responses such as button pressing, the P300 appears to reflect only this stimulus evaluation time and not the time required to translate the decision into the physical response (such as which finger to use). The P300 also has the useful property of being larger in response to rare stimuli. The amplitude of the P300 therefore gives information about how the person is categorizing the stimuli and how rare the stimuli are considered to be subjectively.

Given this neuroscientific background, illustrative embodiments of the invention will now be described.

In accordance with principles of the invention, appropriate sequences that contain public and secret elements (pictograms, sounds, etc.) and logic that is, in part, a shared secret are provided. In an authentication session, the user is challenged by a test sequence while his EEG signal is recorded via two or more electrodes from the scalp (perhaps mounted on a headphone-like frame, helmet, etc.). Any conventional system for obtaining EEG signals from the subject can be employed. By way of example only, a system that can be employed is described in Fish & Spehlmann, "EEG Primer," Elsevier, $3^{rd}$ Edition, Dec. 17, 1999, the disclosure of which is incorporated by reference herein. However, the invention is not limited to any particular EEG collecting system.

As with any other automated authentication method, the process involves two stages: the enrollment stage (initial creation of a user model/account) and the authentication stage (process of sampling and testing for authenticity). In accordance with principles of the invention, we distinguish two types of enrollment: a) enrollment with explicitly defined authentication logic (supervised enrollment); and b) enrollment with implicitly defined logic (unsupervised enrollment). In the following description, the term "logic" refers to the knowledge of a certain type of relationship between elements, or of rules that govern their sequences. The logic represents the shared secret in the overall authentication scheme, and can be stated explicitly, e.g., "white can follow red but red cannot follow white," or implicitly, e.g., user's personal (and secret) explanation of a certain sequence of pictures reflected in the P300 response.

In a supervised enrollment embodiment, a genuine user is familiarized with certain logic and elements of the sequence (i.e., the shared secret), such that the logic and elements of the sequence will not generate P300 when presented during authentication. An imposter will not be familiar with that logic and the elements of the sequence and hence will produce one or several P300 at particular places in the authentication sequence. An automated imposter-detection apparatus analyzes the EEG/P300 signals to decide whether an impostor attack occurred. Such a supervised enrollment embodiment will be described below in the context of FIG. 2A.

Figure 2A:
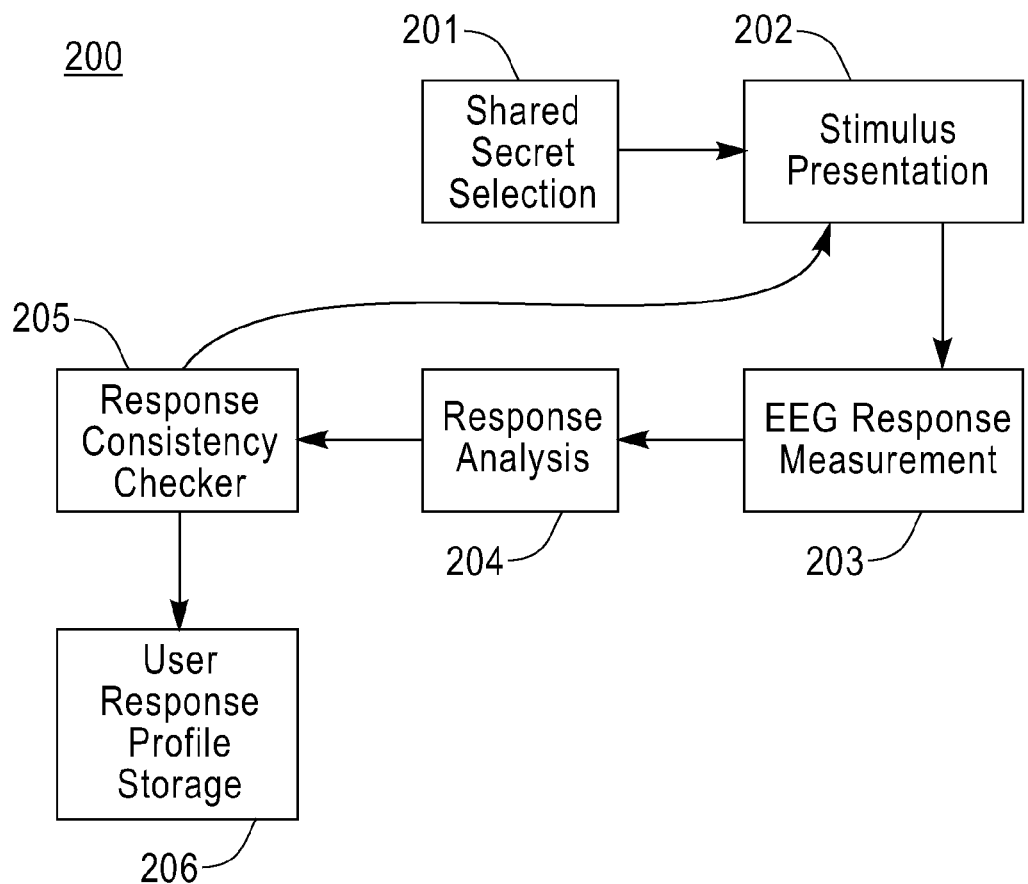
FIG. 2A shows an enrollment system/methodology with explicit statement of logic (supervised enrollment) according to an embodiment of the invention.

FIG. 2A shows the functional blocks in enrollment stage 200 with explicit statement of the logic. The system first selects the logic and elements of the sequence (step 201). The selection can be automatically done, or it can be specified by a system administrator. A genuine user (subject to be enrolled) is presented a statement of the logic (step 202), e.g., in verbal form "white can follow red, but red cannot follow white," or in an appropriate pictorial form showing examples uniquely explaining the given rule. It is to be understood that, in supervised enrollment, the genuine user is made aware of the selected stimulus before the EEG is measured and analyzed. The user's EEG response to the stimulus presentation is measured (step 203). The response is analyzed (step 204). Again, analysis can be performed via conventional automated EEG analysis techniques, or it can be performed via a system administrator reading EEG response results. A consistency check can be performed on the user response (step 205), again this can be automated or not. From the analysis and consistency check, a user response profile can be created and stored (step 206).

Thus, in one embodiment, the user can be optionally presented a set of validation examples in a session during which the EEG signal is recorded, analyzed automatically and stored. Based on the analysis (P300 aligned with the test samples), the enrollment may be finished, or repeated (i.e., consistency checker block 205 feeds back to stimulus presentation block 202) depending on whether the user produced consistent and correct P300 responses.

Thus, advantageously, when the enrolled user is later presented (i.e., during authentication) with the same shared secret that was used to enroll him, such presentation will not generate a P300 signal.

Figure 2B:
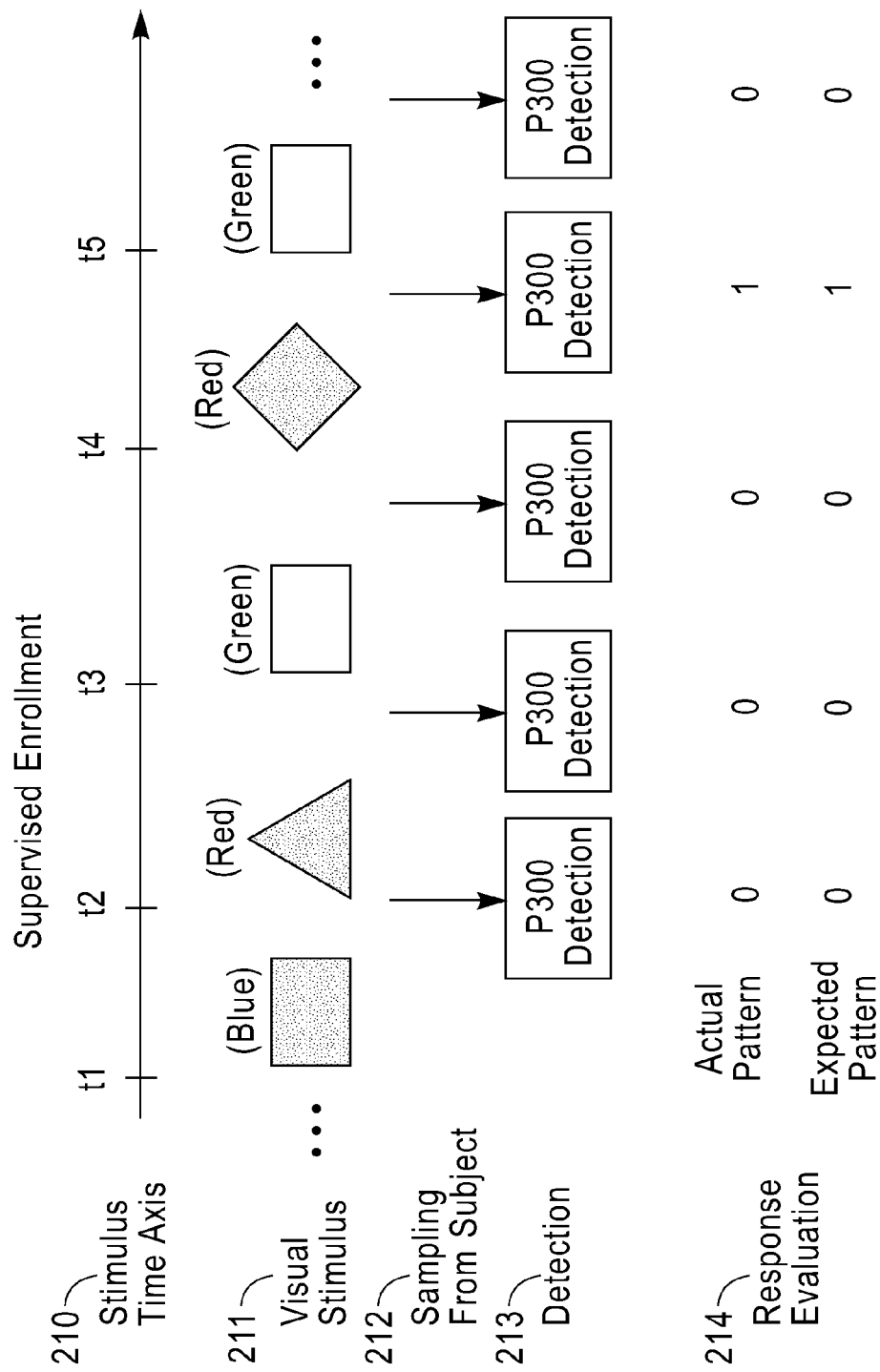
FIG. 2B shows an example of supervised enrollment according to an embodiment of the invention.

FIG. 2B illustrates an example of supervised enrollment. It is assumed that the user is first informed of the rule, in this example, "red can only follow blue, all other colors can appear at any time, and shapes play no role." The user may be informed of the explicit rule audibly or visually. Then, the user is presented with one piece of visual stimulus (211) at each time instance t1, t2, . . . (210). The visual stimulus is in the form of a shape (rectangle, triangle) that is colored (blue, red, green).

Note that since the attached figures are in black and white format rather than in color, the color of the shape that is actually presented to the user is parenthetically noted above the shape. However, it is to be understood that the display used to present the visual stimulus to the user presents the shape in the indicated color.

EEG readings (samplings) are taken from the user (212). P300 detection (213) is performed after each stimulus is presented to the user. The detection response is then evaluated (214).

As illustrated, at time instance t1, the user is presented with a blue shape. Since nothing here violates the explicit rule ("red can only follow blue, all other colors can appear at any time, and shapes play no role"), no P300 signal is detected. At time instance t2, the user is presented with a red shape. But since the red shape followed a blue shape, as expected by the user based on his awareness of the explicit rule, no P300 signal is detected. A similar result is determined in response to the visual stimulus presented at time instance t3.

However, at time instance t4, the user is presented with a red shape. This violates the explicit rule that red can only follow blue. Therefore, since this is an unexpected occurrence or a surprise to the user, a P300 signal is detected in the user's EEG.

As explained above, a consistency check can be performed on the user responses. From the analysis (response evaluation) and consistency check, a user response profile is created and stored for later use in an authentication process.

Turning now to an unsupervised enrollment embodiment, the logic specific to the genuine user is derived automatically in an unsupervised fashion from an enrollment session with the user, wherein the user is presented various stimuli sequences and his/her EEG signal responses related to P300 are analyzed. The automatically derived logic is then applied as in the above supervised case during authentication. Such an unsupervised enrollment embodiment will be described below in the context of FIG. 3A.

Figure 3A:
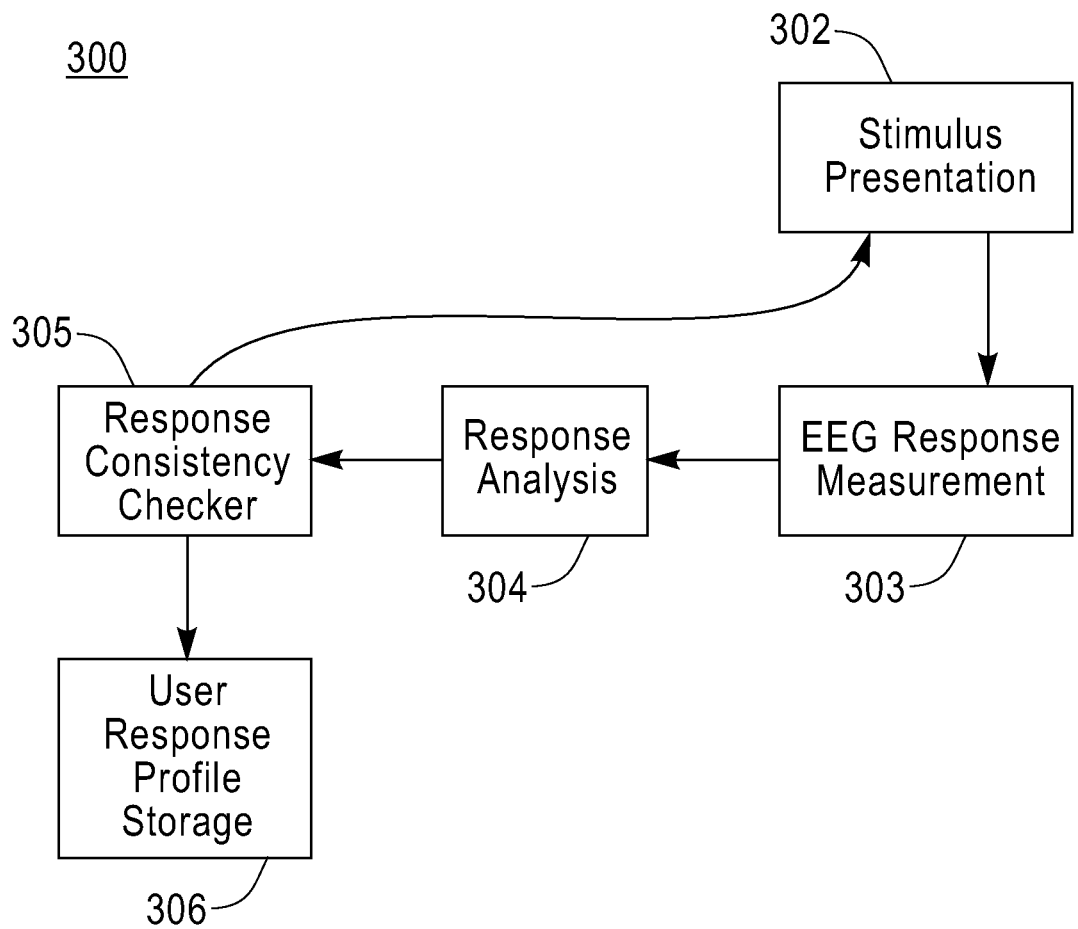
FIG. 3A shows an enrollment system/methodology with implicitly determined logic (unsupervised enrollment) according to an embodiment of the invention.

FIG. 3A shows the functional blocks in enrollment stage 300 with implicitly determined logic. It is to be understood that the main difference between supervised enrollment and unsupervised enrollment is that, in the latter, the genuine user is not made aware of the selected stimulus before EEG is measured and analyzed. A genuine user (subject to be enrolled) is presented (step 301) a sufficiently rich example of stimuli sequence allowing for a variety of interpretations, e.g., a sequence allowing for choosing a rule "white follows red" but also another valid rule "lighter color element follows after two darker elements," etc. The P300 response is measured (step 303) analyzed (step 304) and stored (step 306) along with the information about the specific stimulus sequence. The user can be optionally asked to repeat a set of validation sessions during which the response is analyzed for consistency (step 305) with the previously stored data.

Figure 3B:
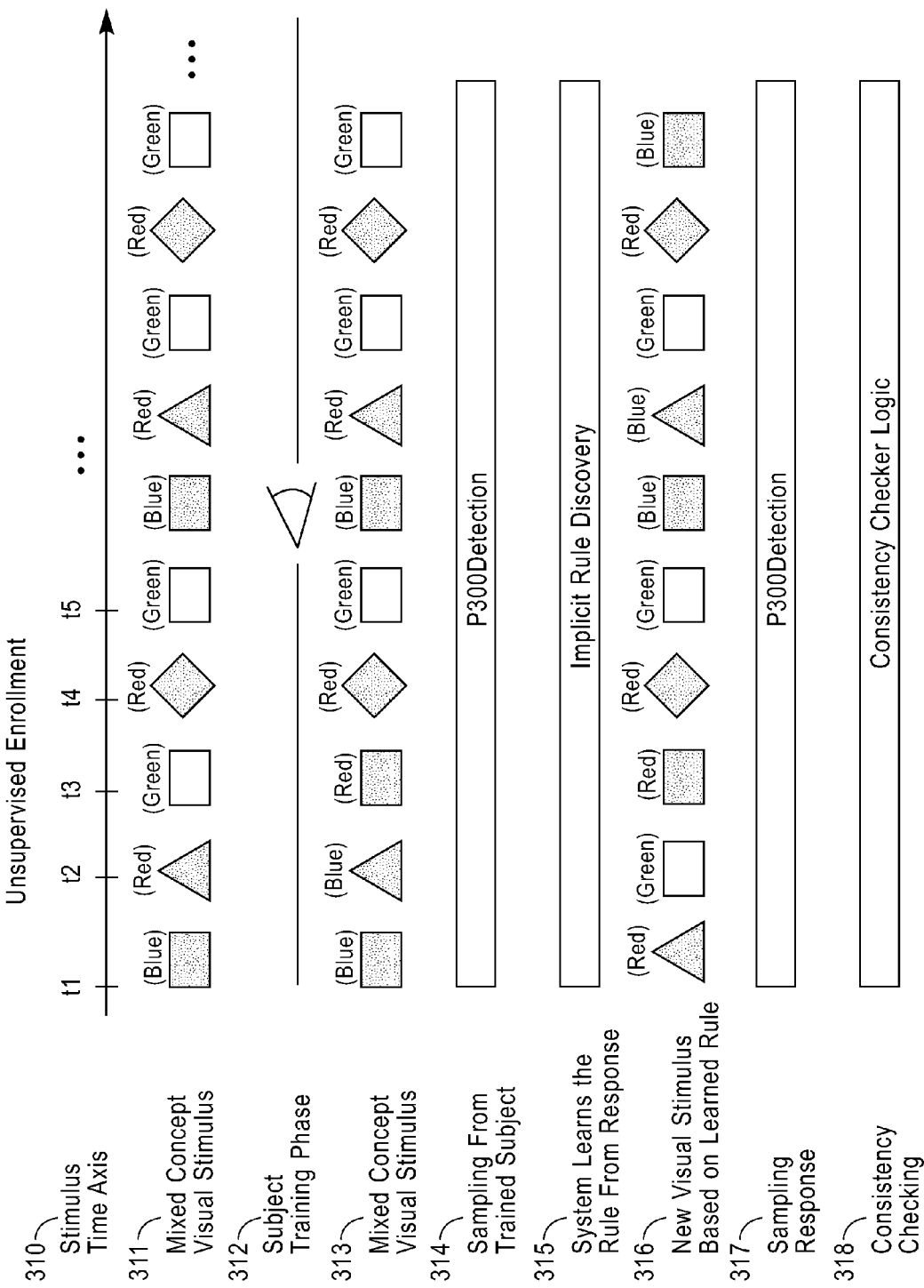
FIG. 3B shows an example of unsupervised enrollment according to an embodiment of the invention.

FIG. 3B illustrates an example of supervised enrollment. The user is presented with a multi-concept stimuli sequence (311), wherein one piece of visual stimulus is presented at each time instance t1, t2, . . . (310). Again, the visual stimulus is in the form of a shape (rectangle, triangle) that is colored (blue, red, green). Note again that the color of the shape that is actually presented to the user is parenthetically noted above the shape due to the black and white nature of the figures. In a user (subject) training phase (312), the user selects on of the concepts represented in the multi-concept stimuli sequence. For example, "red can take any shape, all other colors must be a rectangle." The rule selection is discovered (315) by the system by presenting another sequence (313) with various rule violations and measuring the P300 response (314). Once the rule is learned, enrollment may proceed as follows: new visual stimulus is presented to the user based on the learned rule (316) and P300 detection is performed (317). Responses and rule discovery can be checked for consistency (318) as explained above. From the analysis (response evaluation) and consistency check, a user response profile is created and stored for later use in an authentication process.

Figure 4A:
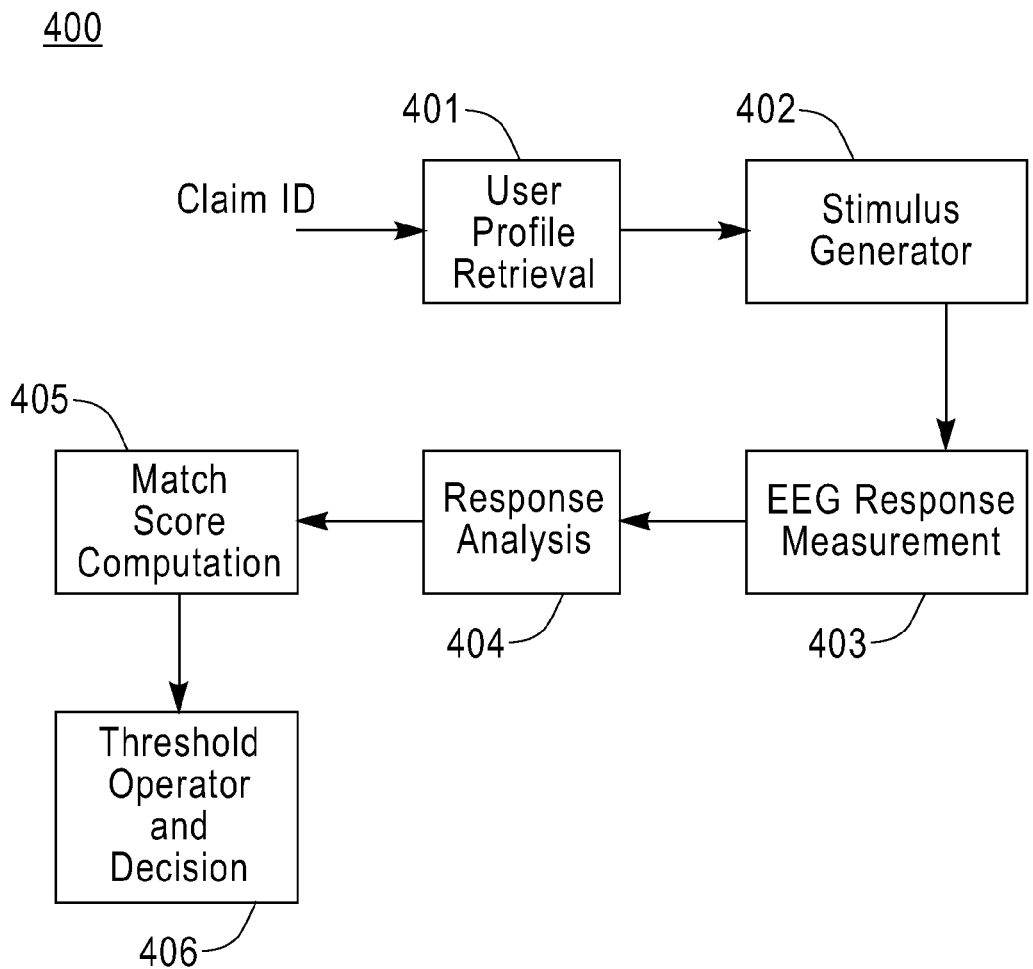
FIG. 4A shows an authentication system/methodology according to an embodiment of the invention.

An authentication process is shown schematically in FIG. 4. A user (subject to be authenticated) is asked to provide a claim identifier, uniquely identifying the account. The system retrieves account-specific data related to the authentication process (step 401).

In the case of an explicit (supervised) enrollment, the system will retrieve the stored logic associated with that user, i.e., represented by the set of one or more rules used during enrollment of that user. The system will then generate an appropriate stimulus sequence (step 402) to be presented to the user employing the defined (and secret) logic as well as optionally employing other reference logic that may be obvious to a general user. The sequence may be different from the one used during enrollment, i.e., a different sequence is a sequence consisting of items following the same logic as in enrollment (interleaved with items not following the logic, for reference), but not necessarily being exactly the same in terms of presentation (e.g., logic="green object can follow red object," but which object is a variable that changes from sequence to sequence).

In the case of implicit (unsupervised) enrollment, the system retrieves the stored stimulus sequence used in the enrollment stage, and presents the stimulus to the user.

During the stimulus presentation, the system records the EEG signal (step 403) and detects P300 response (step 404), which are time-aligned with the presentation (in a manner similar to the time-alignment shown in the enrollment examples of FIGS. 2B and 3B).

A comparison of the measured response to the stored information from enrollment is performed (steps 405 and 406) as follows:

In the case of explicit logic, a score corresponding to the number of consistently placed P300 responses (consistent with respect to the logic) is calculated.

In the case of implicit logic, a score corresponding to the number of time-correctly placed P300 responses (with respect to the enrollment response) is calculated.

The authentication process is finalized by subjecting the resulting score, S, to an authentication threshold, t, such that the user is positively authenticated if S>t and rejected otherwise. A score can be calculated, for instance, as a negative cumulative distance obtained using a dynamic time-warping technique.

Figure 4B:
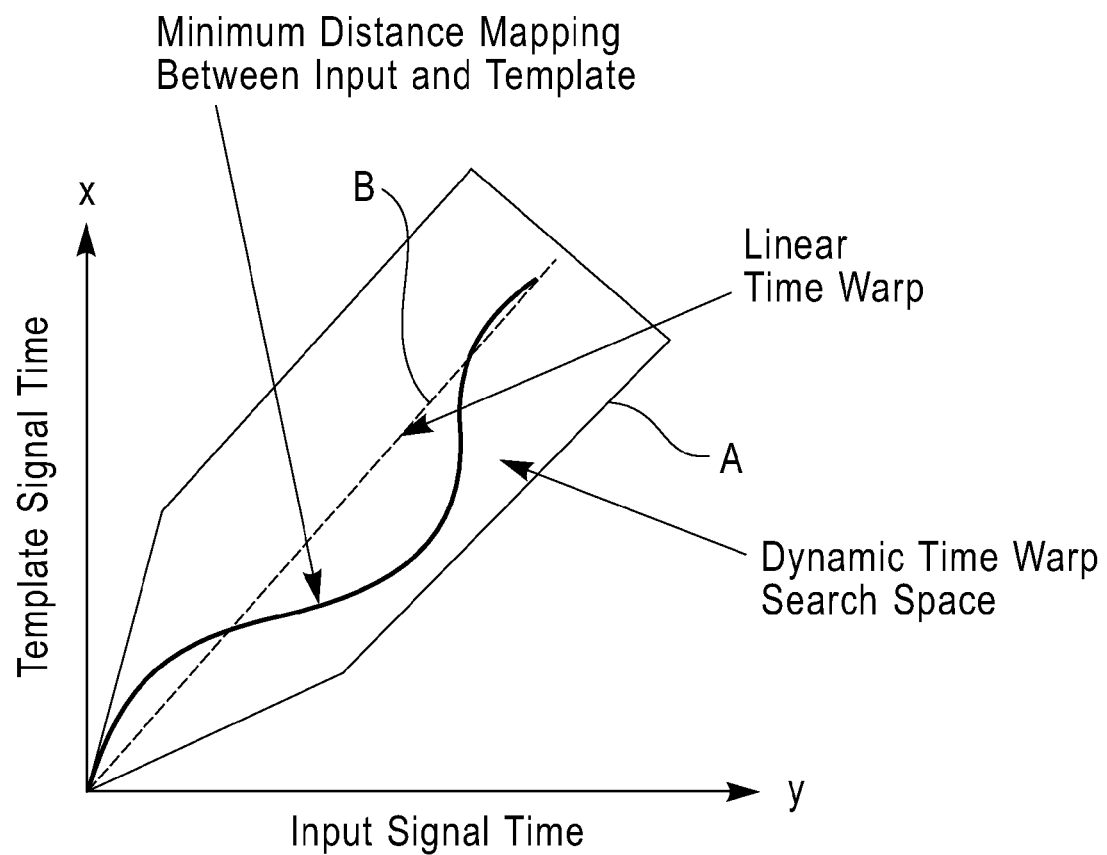
FIG. 4B shows a dynamic time-warping technique according to an embodiment of the invention.

FIG. 4B shows a dynamic time-warping technique that may be employed. Axes x and y correspond to the two signals to which the technique is applied. In our case, the "template signal" represents the result set obtained during enrollment and the "input signal" represents the result set obtained in real-time during the user's attempt to be authenticated. As shown, reference letter A refers to the dynamic time warp search space, reference letter B refers to the linear time warp, and reference letter C refers to the minimum distance mapping between the input signal and the template signal. Thus, the x axis and the y axis correspond to the two signals (template and input) being aligned. One of ordinary skill in the art will realize how dynamic time-warping technique is applied in the context of the principles of the invention disclosed herein.

It is to be understood that the methods described above are not restricted to using color stimuli as the form of perceptory stimuli, but cover any pictorial (e.g., photographs) as well as auditory (sounds) stimuli and their fusion. Furthermore, given the principles of the invention illustratively described herein, enrollment and authentication processes can be realized that utilize sensory presentation methods other than the perceptory modes illustrated herein.

Figure 5:
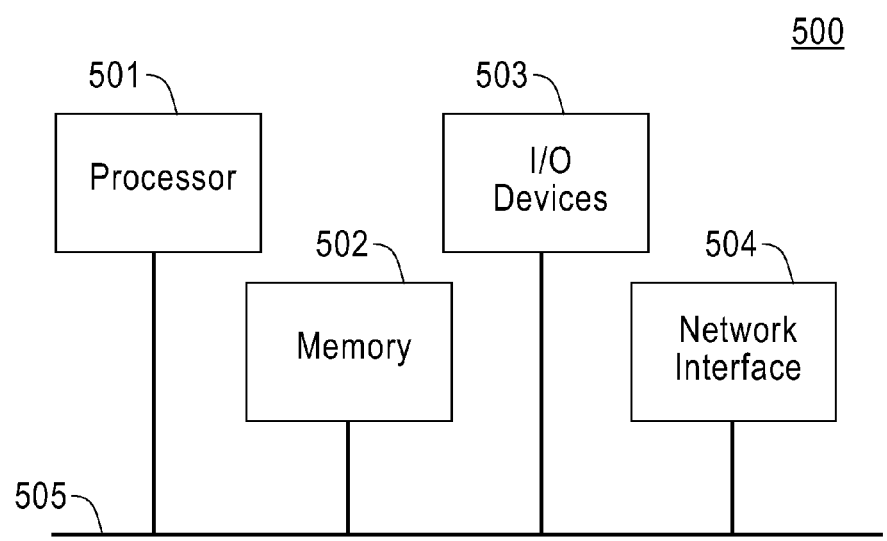
FIG. 5 shows a computing system for implementing enrollment and authentication systems/methodologies according to an embodiment of the invention.

FIG. 5 shows a computing system for implementing enrollment and authentication systems/methodologies according to an embodiment of the invention. That is, FIG. 5 illustrates a computing system in accordance with which one or more components/steps of the enrollment/authentication techniques (e.g., components and methodologies described above in the context of FIGS. 2A through 4B) may be implemented, according to an embodiment of the invention. It is to be understood that the individual components/steps may be implemented on one such computer system or on more than one such computer system. In the case of an implementation on a distributed computing system, the individual computer systems and/or devices may be connected via a suitable network, e.g., the Internet or World Wide Web. However, the system may be realized via private or local networks. In any case, the invention is not limited to any particular network.

As shown, computing system 500 includes processor 501, memory 502, input/output (I/O) devices 503, and network interface 504, coupled via a computer bus 505 or alternate connection arrangement.

It is to be appreciated that the term "processor" as used herein is intended to include any processing device, such as, for example, one that includes a CPU and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. The memory may be considered an example of an article of manufacture comprising a computer readable storage medium containing one or more programs which when executed by a computer implement the steps of the methodologies described herein.

In addition, the phrase "input/output devices" or "I/O devices" as used herein is intended to include, for example, one or more input devices (e.g., keyboard, mouse, etc.) for entering data to the processing unit, and/or one or more output devices (e.g., display, etc.) for presenting results associated with the processing unit.

Still further, the phrase "network interface" as used herein is intended to include, for example, one or more transceivers to permit the computer system to communicate with another computer system via an appropriate communications protocol.

Accordingly, software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

In any case, it is to be appreciated that the techniques of the invention, described herein and shown in the appended figures, may be implemented in various forms of hardware, software, or combinations thereof, e.g., one or more operatively programmed general purpose digital computers with associated memory, implementation-specific integrated circuit(s), functional circuitry, digital signal processor(s) (DSPs), etc. Given the techniques of the invention provided herein, one of ordinary skill in the art will be able to contemplate other implementations of the techniques of the invention.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for authenticating a user, comprising the steps of:
   receiving a claim from an individual claiming to be an enrolled user;
   retrieving a stored electroencephalographic response profile associated with the enrolled user, the electroencephalographic response profile being generated as a result of a supervised enrollment process based on a shared secret, wherein the shared secret comprises a sequence of visual elements which follows an explicit rule known by the enrolled user during the supervised enrollment process, wherein the explicit rule specifies at least one of a relationship between the visual elements and an allowed sequence of the visual elements;
   presenting perceptory stimuli to the individual, the perceptory stimuli comprising the shared secret;
   obtaining at least one electroencephalographic response from the individual in response to the perceptory stimuli comprising said shared secret presented to the individual; and
   authenticating the individual's claim as being the enrolled user based on the obtained electroencephalographic response, wherein authenticating comprises;
      detecting a pattern of P300 event-related potentials in the obtained electroencephalographic response;
      comparing the detected pattern of P300 event-related potentials with an expected pattern of P300 event-related potentials as provided by the stored electroencephalographic response profile associated with the enrolled user, wherein an unexpectedly produced P300 event-related potential in the detected pattern is indicative of an imposter;

determining an authentication score based on results of said comparing; and comparing the determined authentication score to a predetermined authentication threshold value to positively authenticate the individual as being the claimed enrolled user when the authentication score meets or exceeds the predetermined authentication threshold or to reject the individual as an imposter when the authentication score does not meet or exceed the predetermined authentication threshold.

2. The method of claim 1, further comprising performing the supervised enrollment process, wherein the supervised enrollment process comprises:

presenting a set of perceptory stimuli to a user to be enrolled, wherein the set of perceptory stimuli comprises one or more sequences of visual elements that follow the explicit rule and one or more sequences of visual elements that violate the explicit rule, and wherein the user is informed of the explicit rule before being presented with the set of perceptory stimuli;

recording a set of electroencephalographic responses of the user in response to the set of perceptory stimuli presented to the user, wherein the set of electroencephalographic responses comprises at least one P300 event-related potential which corresponds to the occurrence of a violation of the explicit rule; and analyzing the set of recorded electroencephalograph responses to generate a set of results which are stored as part of the electroencephalographic response profile of the enrolled user.

3. The method of claim 2, further comprising the step of confirming the consistency of the set of results by repeating the supervised enrollment process.

4. The method of claim 1, wherein the authentication score comprises a negative cumulative distance measure obtained using a dynamic time-warping process.

5. The method of claim 1, wherein authenticating comprises time-aligning the detected pattern of P300 event-related potentials with the perceptory stimuli presented to the individual.

6. The method of claim 1, wherein a P300 event-related potential comprises a prominent peak detectable in an electroencephalographic signal after about 300 milliseconds (ms) following a perceptory stimulus.

7. An article of manufacture comprising a non-transitory computer readable storage medium comprising program instructions which, when executed by a computer, causes the computer to execute a method comprising:

receiving a claim from an individual claiming to be an enrolled user;

retrieving a stored electroencephalographic response profile associated with the enrolled user, the electroencephalographic response profile being generated as a result of a supervised enrollment process based on a shared secret, wherein the shared secret comprises a sequence of visual elements which follows an explicit rule known by the enrolled user during the supervised enrollment process, wherein the explicit rule specifies at least one of a relationship between the visual elements and an allowed sequence of the visual elements;

presenting peceptory stimuli to the individual, the peceptory stimuli comprising the shared secret;

obtaining at least one electroencephalographic response from the individual in response to the perceptory stimuli comprising said shared secret presented to the individual; and authenticating the individual's claim as being the enrolled user based on the obtained electroencephalographic response, wherein authenticating comprises:

detecting a pattern of P300 event-related potentials in the obtained electroencephalographic response;

comparing the detected pattern of P300 event-related potentials with an expected pattern of P300 event-related potentials as provided by the stored electroencephalographic response profile associated with the enrolled user, wherein an unexpectedly produced P300 event-related potential in the detected pattern is indicative of an imposter;

determining an authentication score based on results of said comparing; and comparing the determined authentication score to a predetermined authentication threshold value to positively authenticate the individual as being the claimed enrolled user when the authentication score meets or exceeds the predetermined authentication threshold or to reject the individual as an imposter when the authentication score does not meet or exceed the predetermined authentication threshold.

8. A method for authenticating a user, comprising the steps of:

receiving a claim from an individual claiming to be an enrolled user;

retrieving a stored electroencephalographic response profile associated with the enrolled user, the electroencephalographic response profile being generated as a result of an unsupervised enrollment process based on an implicit rule, said implicit rule being learned from electroencephalographic signals obtained in response to the user being presented with one or more training sequences of visual elements, wherein the implicit rule specifies at least one of a relationship between the visual elements and an allowed sequence of the visual elements;

presenting perceptory stimuli to the individual, the perceptory stimuli comprising a sequence of visual elements that follow the implicit rule;

obtaining at least one electroencephalographic response from the individual in response to the perceptory stimuli presented to the individual; and authenticating the individual's claim as being the enrolled user based on the obtained electroencephalographic response, wherein authenticating comprises:

detecting a pattern of P300 event-related potentials in the obtained electroencephalographic response;

comparing the detected pattern of P300 event-related potentials with an expected pattern of P300 event-related potentials as provided by the stored electroencephalographic response profile associated with the enrolled user, wherein an unexpectedly produced P300 event-related potential in the detected pattern is indicative of an imposter;

determining an authentication score based on results of said comparing; and comparing the determined authentication score to a predetermined authentication threshold value to positively authenticate the individual as being the claimed enrolled user when the authentication score meets or exceeds the predetermined authentication threshold or to reject the individual as an imposter when the authentication score does not meet or exceed the predetermined authentication threshold.

9. The method of claim 8, further comprising performing the unsupervised enrollment process, wherein the unsupervised enrollment process comprises:
   presenting a set of training perceptory stimuli to a user to be enrolled, wherein the set of training perceptory stimuli comprises one or more training sequences of visual elements;
   recording a set of electroencephalographic responses generated in response to the user being presented with the one or more training sequences of visual elements;
   analyzing the set of recorded electroencephalographic responses to learn at least one rule;
   presenting, to the user, at least one perceptory stimuli that is based on the at least one learned rule;
   recording a second set of electroencephalographic responses generated in response to the user being presented with the at least one perceptory stimuli based on the at least one learned rule; and
   using the recorded second set of electroencephalographic responses to perform a consistency check for the at least one learned rule.

10. The method of claim 9, wherein during the unsupervised enrollment process, the user is not informed of the one or more rules that are learned from the training set of perceptory stimuli.

11. The method of claim 9, wherein during the unsupervised enrollment process, the user selects one of the one or more implicit rules that are learned from the training set of perceptory stimuli.

12. The method of claim 8, wherein the authentication score comprises a negative cumulative distance measure obtained using a dynamic time-warping process.

13. The method of claim 8, wherein authenticating comprises time-aligning the detected pattern of P300 event-related potentials with the perceptory stimuli presented to the individual.

14. The method of claim 8, wherein a P300 event-related potential comprises a prominent peak detectable in an electroencephalographic signal after about 300 milliseconds (ms) following a perceptory stimulus.

15. An article of manufacture comprising a non-transitory computer readable storage medium comprising program instructions which, when executed by a computer, causes the computer to execute a method comprising:
   receiving a claim from an individual claiming to be an enrolled user;
   retrieving a stored electroencephalographic response profile associated with the enrolled user, the electroencephalographic response profile being generated as a result of an unsupervised enrollment process based on an implicit rule, said implicit rule being learned from electroencephalographic signals obtained in response to the user being presented with one or more training sequences of visual elements, wherein the implicit rule specifies at least one of a relationship between the visual elements and an allowed sequence of the visual elements;
   presenting perceptory stimuli to the individual, the perceptory stimuli comprising a sequence of visual elements that follow the implicit rule;
   obtaining at least one electroencephalographic response from the individual in response to the perceptory stimuli presented to the individual; and
   authenticating the individual's claim as being the enrolled user based on the obtained electroencephalographic response, wherein authenticating comprises:
      detecting a pattern of P300 event-related potentials in the obtained electroencephalographic response;
      comparing the detected pattern of P300 event-related potentials with an expected pattern of P300 event-related potentials as provided by the stored electroencephalographic response profile associated with the enrolled user, wherein an unexpectedly produced P300 event-related potential in the detected pattern is indicative of an imposter;
      determining an authentication score based on results of said comparing; and
      comparing the determined authentication score to a predetermined authentication threshold value to positively authenticate the individual as being the claimed enrolled user when the authentication score meets or exceeds the predetermined authentication threshold or to reject the individual as an imposter when the authentication score does not meet or exceed the predetermined authentication threshold.

16. An apparatus, comprising:
   a memory configured to store program instructions; and
   a processor coupled to the memory and configured to execute the stored program instructions to execute a process to authenticate a user, the process comprising
   receiving a claim from an individual claiming to be an enrolled user;
   retrieving a stored electroencephalographic response profile associated with the enrolled user, the electroencephalographic response profile being generated as a result of a supervised enrollment process based on a shared secret, wherein the shared secret comprises a sequence of visual elements which follows an explicit rule known by the enrolled user during the supervised enrollment process, wherein the explicit rule specifies at least one of a relationship between the visual elements and an allowed sequence of the visual elements;
   presenting perceptory stimuli to the individual, the perceptory stimuli comprising the shared secret;
   obtaining at least one electroencephalographic response from the individual in response to the perceptory stimuli comprising said shared secret presented to the individual; and
   authenticating the individual's claim as being the enrolled user based on the obtained electroencephalographic response, wherein authenticating comprises:
      detecting a pattern of P300 event-related potentials in the obtained electroencephalographic response;
      comparing the detected pattern of P300 event-related potentials with an expected pattern of P300 event-related potentials as provided by the stored electroencephalographic response profile associated with the enrolled user, wherein an unexpectedly produced P300 event-related potential in the detected pattern is indicative of an imposter;
      determining an authentication score based on results of said comparing; and
      comparing the determined authentication score to a predetermined authentication threshold value to positively authenticate the individual as being the claimed enrolled user when the authentication score meets or exceeds the predetermined authentication threshold or to reject the individual as an imposter when the authentication score does not meet or exceed the predetermined authentication threshold.

17. The apparatus of claim 16, wherein the process further comprises performing the supervised enrollment process, wherein the supervised enrollment process comprises:
- presenting a set of perceptory stimuli to a user to be enrolled, wherein the set of perceptory stimuli comprises one or more sequences of visual elements that follow the explicit rule and one or more sequences of visual elements that violate the explicit rule, and wherein the user is informed of the explicit rule before being presented with the set of perceptory stimuli;
- recording a set of electroencephalographic responses of the user in response to the set of perceptory stimuli presented to the user, wherein the set of electroencephalographic responses comprises at least one P300 event-related potential which corresponds to the occurrence of a violation of the explicit rule; and
- analyzing the set of recorded electroencephalographic responses to generate a set of results which are stored as part of the electroencephalographic response profile of the enrolled user.

18. The apparatus of claim 16, wherein the authentication score comprises a negative cumulative distance measure obtained using a dynamic time-warping process.

19. The apparatus of claim 16, wherein authenticating comprises time-aligning the detected pattern of P300 event-related potentials with the perceptory stimuli presented to the individual.

20. The apparatus of claim 16, wherein a P300 event-related potential comprises a prominent peak detectable in an electroencephalographic signal after about 300 milliseconds (ms) following a perceptory stimulus.

* * * * *